(12) United States Patent
Nagtegaal et al.

(10) Patent No.: US 12,220,158 B2
(45) Date of Patent: Feb. 11, 2025

(54) CUTTING BLADES FOR BIPOLAR SURGICAL INSTRUMENTS

(71) Applicant: Gyrus Medical Limited, Cardiff (GB)

(72) Inventors: Marno Nagtegaal, Wales (GB); Lewis Jones, Cardiff (GB)

(73) Assignee: GYRUS MEDICAL LIMITD, Cardiff (GB)

( * ) Notice: Subject to any disclaimer, the term of this patent is extended or adjusted under 35 U.S.C. 154(b) by 330 days.

(21) Appl. No.: 16/052,985

(22) Filed: Aug. 2, 2018

(65) Prior Publication Data
US 2019/0038342 A1 Feb. 7, 2019

(30) Foreign Application Priority Data

Aug. 4, 2017 (GB) ..................... 1712541

(51) Int. Cl.
*A61B 18/14* (2006.01)
*A61B 18/00* (2006.01)
*A61B 18/12* (2006.01)

(52) U.S. Cl.
CPC ............... *A61B 18/1445* (2013.01); *A61B 2018/00601* (2013.01); *A61B 2018/00607* (2013.01);
(Continued)

(58) Field of Classification Search
CPC ............ A61B 18/1442; A61B 18/1445; A61B 2018/1452; A61B 2018/1455;
(Continued)

(56) References Cited

U.S. PATENT DOCUMENTS

2002/0188294 A1\* 12/2002 Couture ............. A61B 18/1445
606/171
2011/0009864 A1\* 1/2011 Bucciaglia ............. A61B 17/32
606/52
(Continued)

FOREIGN PATENT DOCUMENTS

DE 4421822 C1 10/1995
EP 1261286 B1 10/2009
(Continued)

OTHER PUBLICATIONS

Smith, Mat; "UK Search Report"; prepared for application No. GB1712541.0; Feb. 7, 2018; 4 pages.

*Primary Examiner* — Thomas A Giuliani
(74) *Attorney, Agent, or Firm* — Oliff PLC (57) ABSTRACT

A substantially planar elongate cutting blade (70) for a bipolar surgical instrument (1) is disclosed. The cutting blade has first and second opposed edges and defining a longitudinal axis, and comprises a proximal end region which extends between the first and second edges over a first distance in a direction perpendicular to the longitudinal axis, and a distal end region defining a cutting surface which extends between the first and second edges over a second distance in a distance perpendicular to the longitudinal axis, the first distance being greater than the second distance. The first and second edges have respective portions that extend at first and second acute angles respectively with respect to the longitudinal axis, and the cutting surface extends transversely at a third angle with respect to the longitudinal axis, the third angle being not equal to the first or second angle.

6 Claims, 11 Drawing Sheets

(52) U.S. Cl.
CPC . *A61B 2018/0063* (2013.01); *A61B 2018/126* (2013.01); *A61B 2018/1452* (2013.01); *A61B 2018/1455* (2013.01)

(58) Field of Classification Search
CPC ........... A61B 2018/00601; A61B 2018/00607; A61B 2018/0063; A61B 2018/126; A61B 17/295; A61B 17/320092
USPC ................. 606/41, 50–52, 170, 171, 205
See application file for complete search history.

(56) References Cited

U.S. PATENT DOCUMENTS

2015/0305802 A1* 10/2015 Stamm ............... A61B 17/3209
  606/167
2016/0338764 A1* 11/2016 Krastins ............. A61B 17/3205

FOREIGN PATENT DOCUMENTS

| EP | 2347725 A1 | 7/2011 |
| EP | 2901950 A1 | 8/2015 |
| EP | 2675383 B1 | 7/2017 |
| WO | WO-2012/112888 A2 | 8/2012 |

* cited by examiner

CUTTING BLADES FOR BIPOLAR SURGICAL INSTRUMENTS

TECHNICAL FIELD OF THE INVENTION

The present invention relates to cutting blades for bipolar surgical instruments.

BACKGROUND OF THE INVENTION

Bipolar surgical instruments are used to clamp and seal tissue, particularly blood vessels, during surgical procedures. Clamping is typically achieved using a pair of opposed jaws that are remotely operable to clamp around the tissue being sealed. Sealing is typically achieved using application of radio frequency energy delivered to the tissue being sealed by electrodes mounted on the opposed jaws of the instrument.

Bipolar surgical instruments may also include cutting blades that enable a surgeon to cut tissue using the same instrument as used for clamping and sealing of that tissue. However, guiding a cutting blade along the jaws of such a bipolar instrument, particularly between curved jaws, is a common problem. Previous solutions to this problem have included increasing the size of the blade that runs along a blade guide within the jaws. However, this increasing blade size, whilst enabling the blade to stay within the track in the jaws, means that the jaws may not be fully closed. In addition, the increasing blade width also makes it difficult to reduce the overall size of the jaws, particularly at the distal end region where it is preferable to have a narrow design for improved tissue access.

Accordingly, it is desirable to provide a cutting blade that addresses such issues.

SUMMARY OF THE INVENTION

Aspects of the present invention are set out in the attached claims.

According to one exemplary aspect, there is provided a substantially planar elongate cutting blade for a bipolar surgical instrument, the cutting blade having first and second opposed edges and defining a longitudinal axis, the cutting blade comprising a proximal end region which extends between the first and second edges over a first distance in a direction perpendicular to the longitudinal axis, a distal end region in which the first and second edges have respective distal end portions that extend at first and second acute angles respectively with respect to the longitudinal axis; and a cutting surface which extends between the distal end portions of the first and second edges over a second distance in a direction perpendicular to the longitudinal axis, the first distance being greater than the second distance, the cutting surface extending transversely at a third angle with respect to the longitudinal axis, the third angle being not equal to the first or second angle.

In one example, the first acute angle is substantially equal to the second acute angle.

In one example, the cutting surface is substantially centred on the longitudinal axis.

In one example, the blade defines an elongate slot therethrough, the slot extending partially along the longitudinal axis between the proximal and distal end regions a blade portion which extends from the distal end of the body portion.

According to another exemplary aspect, there is provided a bipolar surgical instrument comprising a body; an elongate shaft attached to the body, the elongate shaft extending to a distal end; first and second opposed jaws located at the distal end of the elongate shaft, the first jaw being movable with respect to the second jaw between an open position in which the first and second jaws are spaced apart from one another, and a closed position in which the first and second jaws are adjacent one another; an actuation shaft connected with at least the first jaw, the actuation shaft being movable with respect to the body and the elongate shaft between a first position in which the jaws are in the open position, and a second position in which the jaws are in the closed position; an actuation grip movably mounted on the body, and arranged to operate the actuation shaft, the actuation grip having a released position in which the actuation shaft is in the first position, and an engaged position in which the actuation shaft is in the second position; and a blade according to the first aspect, the blade extending through the elongate shaft adjacent the actuation shaft, to the first and second jaws.

Such an instrument may further comprise a blade actuator operable to move the blade between a retracted position and a cutting position.

DETAILED DESCRIPTION OF THE PREFERRED EMBODIMENTS

Figure 1:
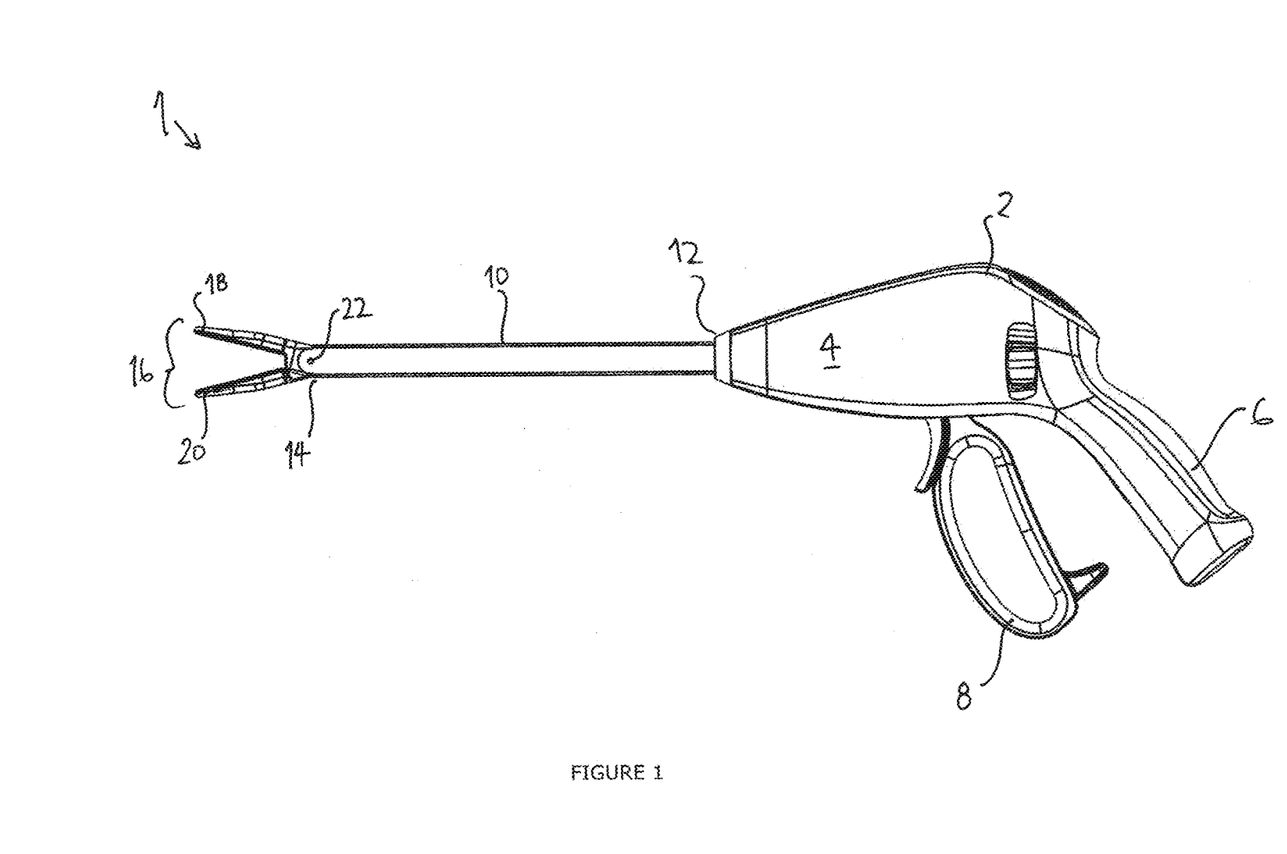
FIGS. 1 and 2 show side views of a bipolar surgical instrument embodying one aspect of the present invention in open and closed positions respectively.
Figure 2:
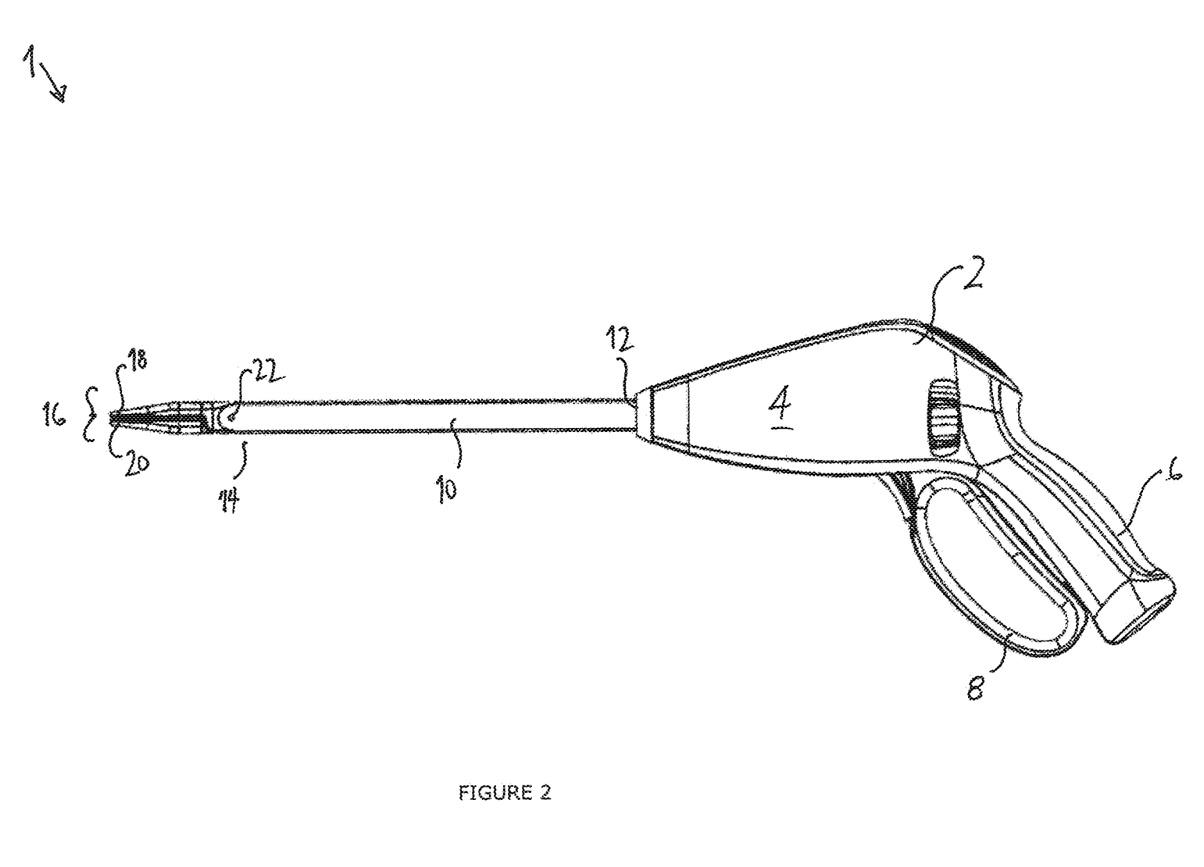

An example bipolar surgical instrument 1 is shown schematically in FIGS. 1 and 2. FIG. 1 illustrates an open position of the instrument 1, and FIG. 2 illustrates a closed position thereof.

The instrument 1 comprises a body 2 having a main housing 4 from which a fixed grip 6 extends. The fixed grip 6 is held during use by the operator of the instrument 1. A movable actuation grip 8 is movably mounted on the main housing 4 of the body 2. An elongate shaft 10 is attached to the main housing 4 of the body 2, and extends from a proximal end 12 at the main housing 4, to a distal end 14 of the shaft 10. The shaft 10 defines a longitudinal axis therealong, and an elongate passage extends from the proximal end 12 to the distal end 14 of the shaft 10. As will be described in more detail below, an actuation shaft extends from the main housing 4 through the passage of the shaft 10.

A pair 16 of opposed jaws are located at the distal end 14 of the shaft 10. The pair 16 of jaws comprises a first jaw 18 and a second jaw 20. In the example of FIGS. 1 and 2, the first and second jaws 18 and 20 are pivotally mounted on a jaw pivot 22. The first and second jaws 18 and 20 are pivotable about the jaw pivot 22, between an open position (as shown in FIG. 1) in which the jaws are separated from one another, and a closed position (as shown in FIG. 2) in which the jaws 18 and 20 are adjacent one another. In another example of a bipolar instrument embodying the present invention, only one of the jaws is movable. In another example, the movable jaw or jaws may be movable in any suitable manner, for example linearly, or in a combination of rotation and linear movement. The exact nature of the movement of the jaws is not important in the context of the present invention.

As will be described in more detail below, the operator of the instrument 1 moves the actuation grip 8 from a first position (shown in FIG. 1) to a second position (shown in FIG. 2) in order to move the jaws 18 and 20 from the open position to the closed position. During an operation, tissue to be sealed is held between the jaws in the closed position for a predetermined time period, with pressure applied by the operator. In an embodiment of the present invention, the pressure exerted by the jaws on the tissue to be sealed is maintained using an actuation assistor.

Figure 3:
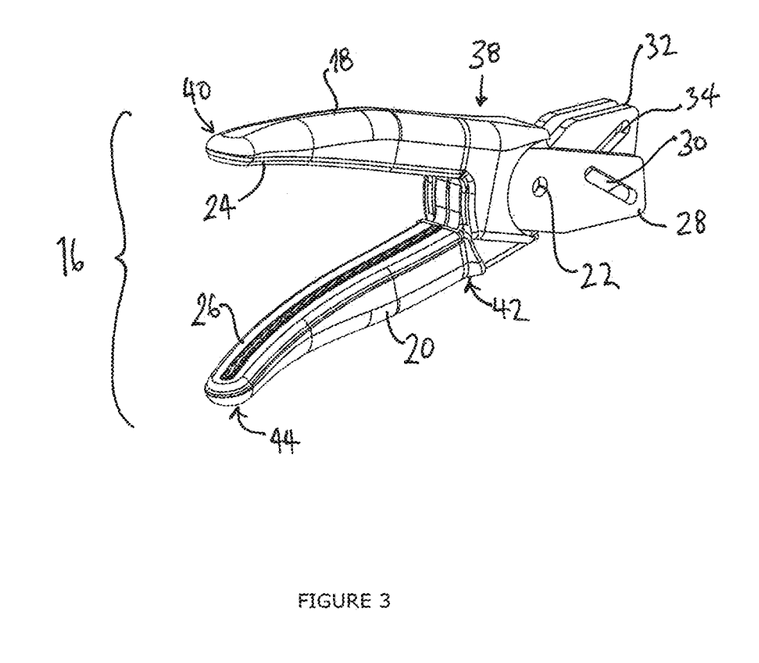
FIGS. 3 and 4 show perspective views of part of the bipolar surgical instrument of FIGS. 1 and 2 in open and closed positions respectively.
Figure 4:
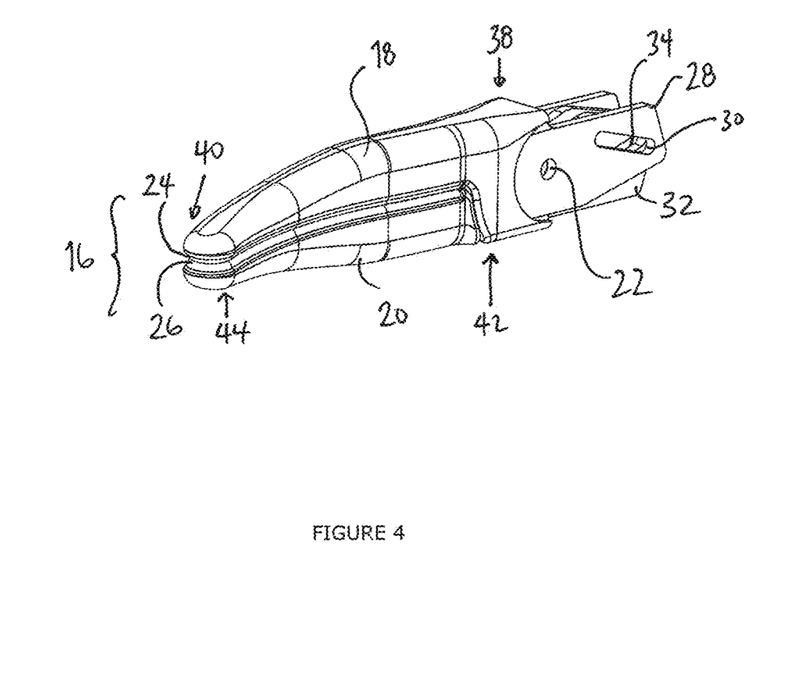
Figure 5:
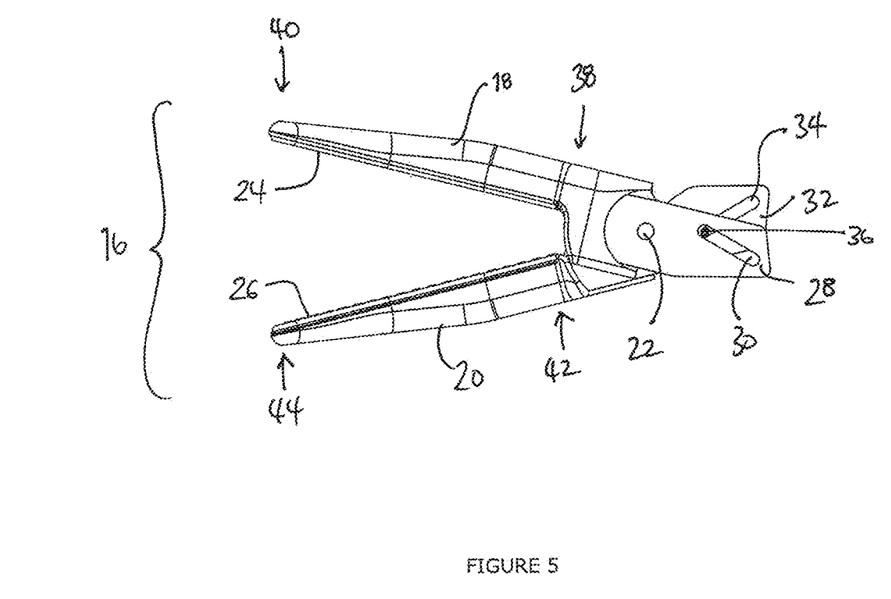
FIGS. 5 and 6 show side views of the part of the bipolar surgical instrument of FIGS. 3 and 4 in open and closed positions respectively.
Figure 6:
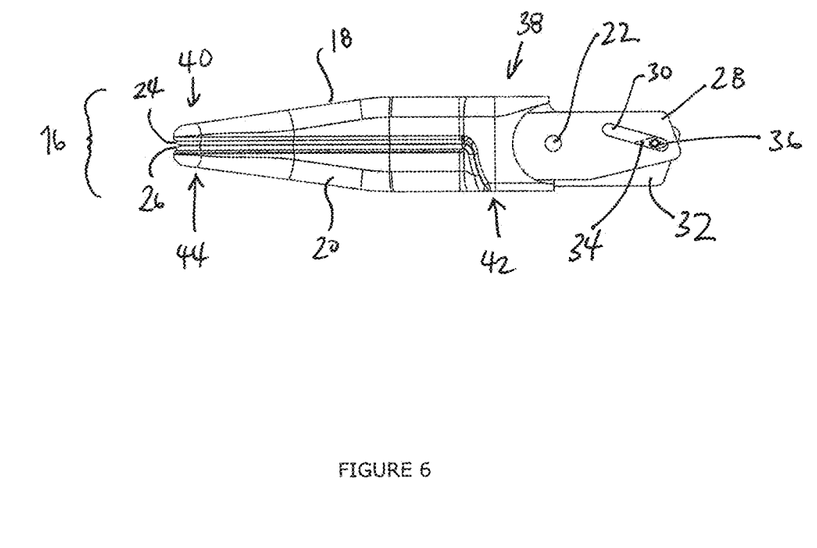
Figure 7:
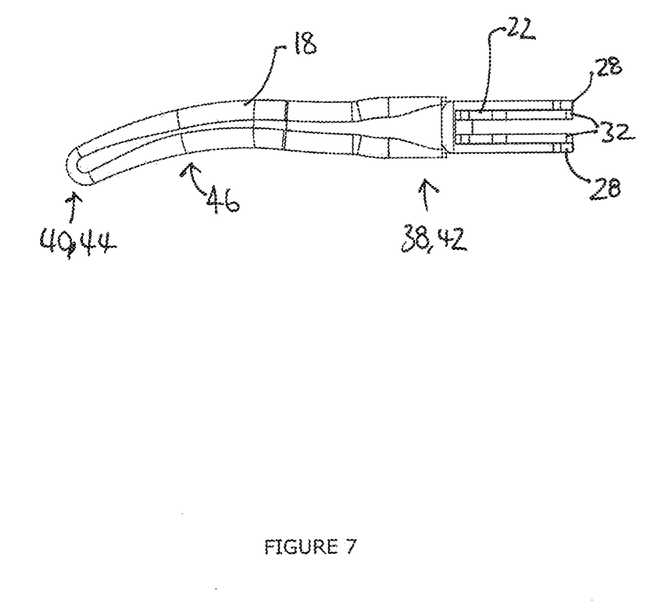
FIG. 7 shows a plan view of the part of the bipolar surgical instrument of FIGS. 3 to 6.

FIGS. 3 to 7 illustrate the pair 16 of jaws 18 and 20. FIGS. 3 and 4 are perspective views of the jaws 18 and 20 in open and closed positions respectively, and FIGS. 5 and 6 are side views of the jaws 18 and 20, again in the open and closed positions respectively. FIG. 7 shows a plan view of the jaws 18 and 20. The first jaw 18 extends from a proximal end 38 thereof to a distal end 40 thereof. Similarly, the second jaw 20 extends from a proximal end 42 thereof to a distal end 44 thereof.

The first and second jaws 18 and 20 have respective inner surfaces which face one another. The first jaw 18 carries a first electrode 24 on the inner surface thereof, and the second jaw 20 carries a second electrode 26 on the inner surface thereof. In the open position shown in FIGS. 3 and 5, the first and second electrodes 24 and 26 are spaced apart from one another. In the closed position shown in FIGS. 4 and 6, the first and second electrodes 24 and 26 are adjacent one another. Each of the first and second electrodes 24 and 26 may be provided by a single electrode, or by any suitable arrangement of a plurality of electrodes.

From the proximal end 38 of the first jaw 18 extends a first actuation member 28 which defines a first actuation slot 30. From the proximal end 42 of the second jaw 20 extends a second actuation member 32 which defines a second actuation slot 34. In the example shown, the first actuation member 28 extends outwardly of the second actuation member 32. The first and second actuation slots 30 and 34 are arranged to overlap one another, and extend at acute angles with respect to the longitudinal axis.

A jaw actuation pin 36 extends through the first and second actuation slots 30 and 34 of the first and second actuation members 28 and 32. The actuation pin 36 engages with the actuation members 28 and 32 in slidable contact. The actuation pin 36 is movable from a first position as shown in FIGS. 3 and 5 to a second position as shown in FIGS. 4 and 6. The first position of the actuation pin 36 corresponds to the open position of the jaws 18 and 20, and the second position of the actuation pin 36 corresponds to the closed position of the jaws 18 and 20. The actuation pin 36 is movable longitudinally with respect to the jaws 18 and 20 and the shaft 10 of the instrument 1. The movement of the actuation pin 36 within the first and second actuation slots 30 and 34 causes the jaws 18 and 22 rotate about the jaw pivot point 22. The actuation pin 36 engages with the actuation members 28 and 32 and drive those members between the open and closed positions. Moving the actuation pin 36 from the first position to the second position moves the jaws 18 and 20 from the open position to the closed position. Moving the actuation pin 36 from the second position to the first position moves the jaws 18 and 20 from the closed position to the open position.

FIG. 7 illustrates the jaws 18 and 20 in plan view. As can be seen from FIG. 7 the jaws extend from the proximal end 38, 42 to the distal end 40, 44, with a curved portion 46. The curved portion 46 curves to one side of a plane in which the actuation members 28 and 32 move. The curved portion 46, as is well known and understood, provides the operator of the instrument 1 with improved usability.

Figure 8:
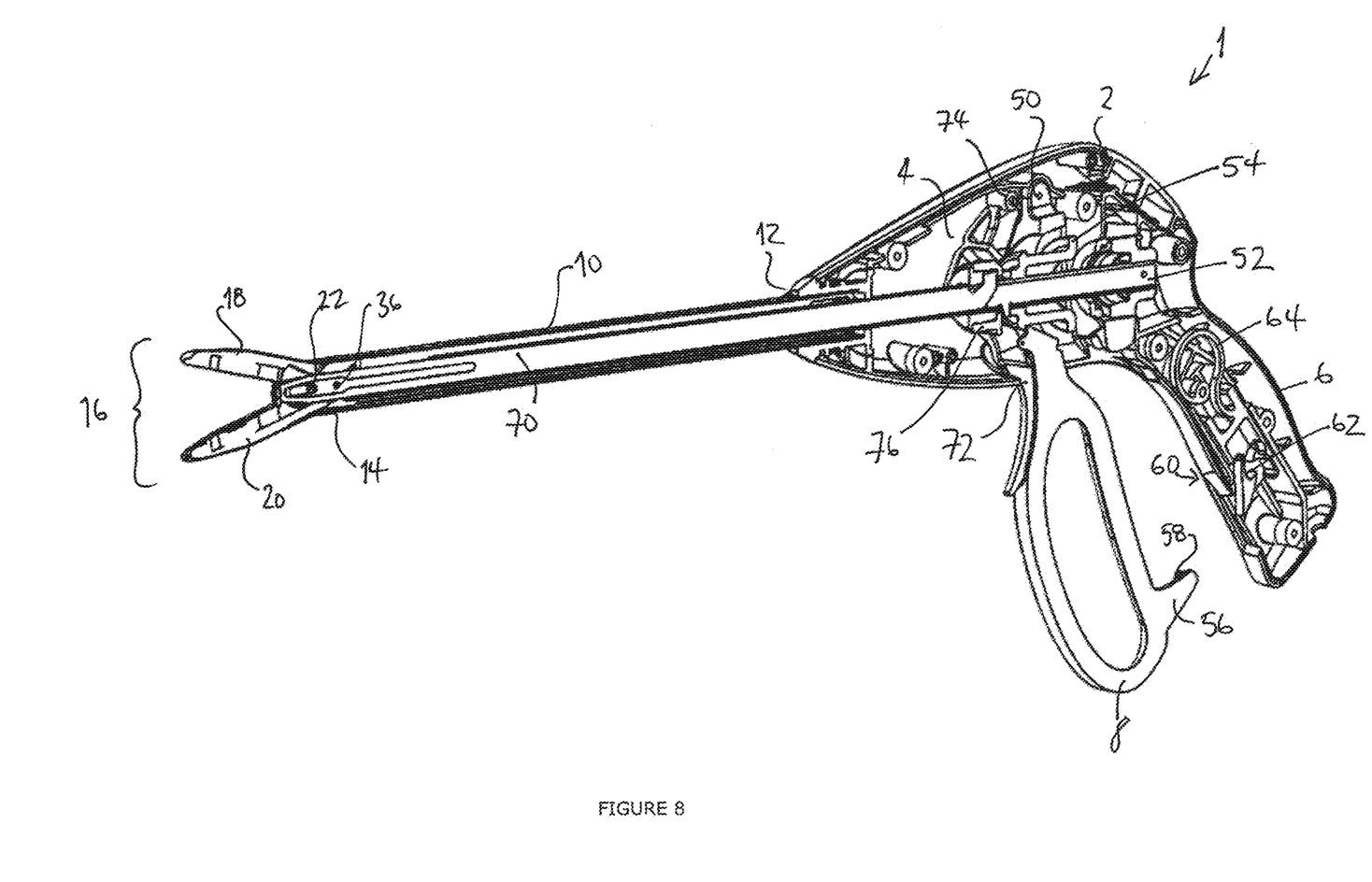
FIG. 8 shows a perspective cross-sectional view of the bipolar surgical instrument of FIGS. 1 and 2.
Figure 9:
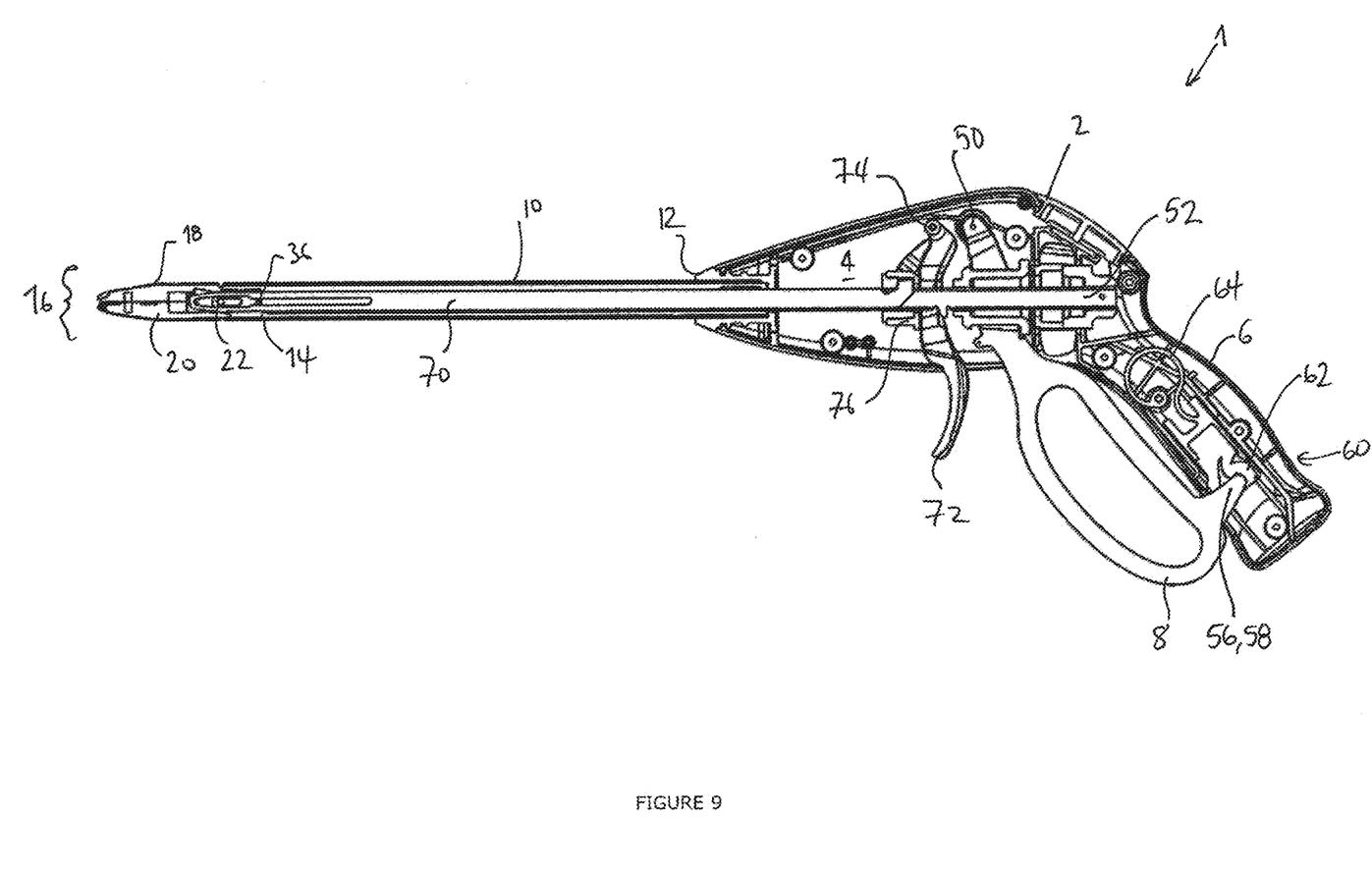
FIG. 9 shows a side cross-sectional view of the bipolar surgical instrument of FIGS. 1 and 2.

FIGS. 8 and 9 illustrate respective perspective and side cross-sectional views of one example of the instrument 1 of FIGS. 1 and 2. FIG. 8 illustrates the instrument in the open position, and FIG. 9 illustrates the instrument in the closed position. It will be appreciated that the instrument shown in FIGS. 8 and 9 is merely exemplary with regard to the present invention. The main housing 4 of the instrument 1 provides an actuation grip pivot 50 on which the actuation grip 8 is mounted. The actuation grip 8 is able to rotate about the actuation grip pivot 50 under the control of the operator between the open and closed positions of the instrument 1. The actuation grip 8 is biased towards the open position by a resilient bias means, such as a spring. An actuation shaft 52 extends from the main housing 4 along the elongate shaft 10, through the passage therein, to the first and second jaws 18 and 20 at the distal end of the elongate shaft 10. The actuation shaft 52 is attached to the actuation grip 8 by way of a shaft retaining portion 54. The shaft retaining portion 54 ensures that as the actuation grip 8 is rotated about the actuation grip pivot 50 that the actuation shaft 52 is moved linearly within the passage of the elongate shaft 10.

The actuation pin 36 is provided at attached to the distal end of the actuation shaft 52. The actuation pin engages with the actuation slots of the first and second jaws 18 and 20, as described above, and is used to move the jaws 18 and 20 between the open and closed positions.

An actuation grip extension 56 extends from the actuation grip 8 at a position remote from the actuation grip pivot 52 the actuation grip extension 56 carries an actuation grip engagement portion 58, which, in this example, extends transversely with respect to the longitudinal axis of the instrument. An actuation assistor 60 is located in the fixed grip 6 of the instrument 1, and defines a receiving aperture 62 for receiving the actuation grip engagement portion 58 therein, when the instrument 1 is in the closed position. As illustrated in FIG. 9, the actuation grip extension 56 extends into the fixed grip 6 when the instrument is in the closed position, such that the engagement portion 58 engages with the actuation assistor 60. The engagement portion is located in the receiving aperture 62 in the closed position.

In addition to the actuation shaft 52, a blade 70 extends through the elongate shaft 10 from the main housing for of the instrument 1 to the distal end of the elongate shaft 10. A blade actuator 72 is rotatably mounted on a blade actuator pivot 74 located in the housing 4. The blade actuator 72 is attached to the blade 70 by means of a blade engaging portion 76, such that rotation of the blade actuator causes linear movement of the blade 70 along the longitudinal axis of the elongate shaft 10. The blade will be described in more detail below.

In operation, the operator of the instrument 1 holds the fixed grip 6 in order to position the jaws 18 and 20 at the appropriate point around a vessel to be sealed. The operator squeezes the actuation grip 8 in order to close the jaws 18 and 20 around the vessel to be sealed. The action of squeezing the actuation grip 8 causes the actuation grip 8 to rotate about the actuation grip pivot 50, thereby moving the shaft retention portion 54 along the longitudinal axis of the instrument 1 in a direction away from the distal end 14 of the elongate shaft 10. This movement of the shaft retention portion 54 causes the actuation shaft 52 to move along the elongate shaft 10 towards the main housing 4. The actuation pin 36 engages the actuation slots 28 and 34, thereby causing the jaws 18 and 20 to rotate into the closed position.

The actuation grip extension 56 is moved into the fixed grip 6, such that the actuation grip engagement portion 58 engages with the actuation assistor 60, and specifically with the receiving aperture 62 in order to retain the actuation grip 8 in the closed position. A resilient member 64 retains the actuation grip engagement portion 58 in the receiving aperture 62 until such time as the operator releases the actuation grip 8.

Whilst in the closed position, a suitable electrical signal is supplied to the electrodes carried by the first and second jaws 18 and 20, so as to seal the vessel being gripped by the jaws 18 and 20. Once sealing has occurred, the actuation grip 8 can be moved by the operator to the open position so as to release the jaws 18 and 20 from around the vessel being sealed, thereby releasing the vessel.

An instrument embodying one aspect of the present invention makes use of a blade 70 which embodies another aspect of the present invention.

Figure 10:
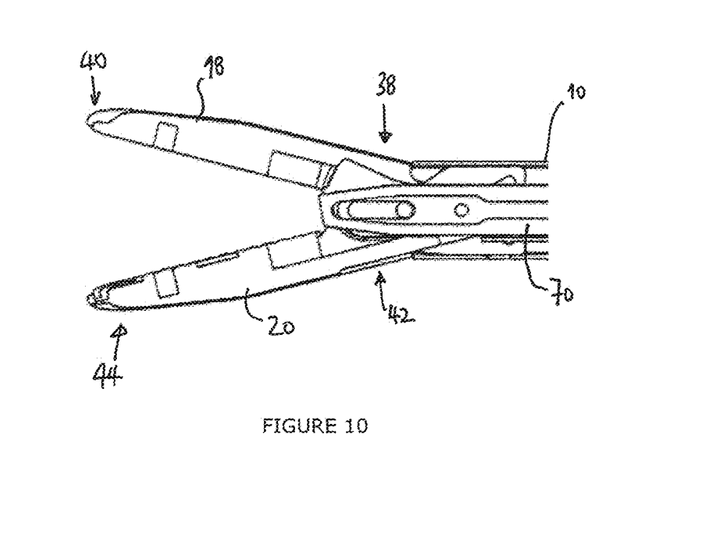
FIG. 10 is a side cross-sectional view of part of a bipolar surgical instrument embodying one aspect of the present invention in an open position illustrating a blade embodying another aspect of the present invention.
Figure 11:
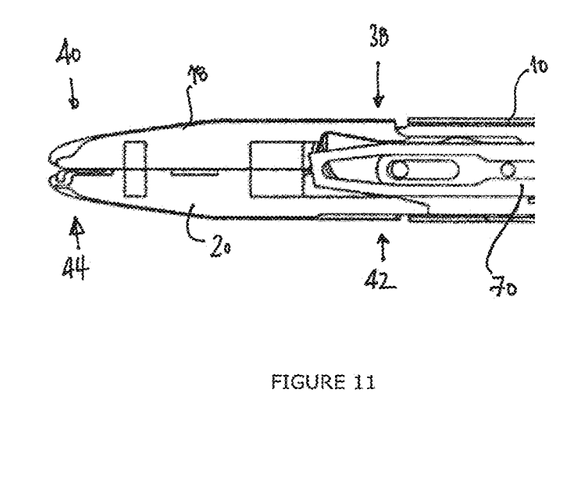
FIG. 11 is a side cross-sectional view of the part of FIG. 10 in a closed position.

FIGS. 10 to 15 illustrate a blade embodying another aspect of the present invention, and the location of such a blade within the jaws of an instrument embodying the present invention. FIGS. 10 and 11 illustrate the jaws 18 and 20 in open and closed positions respectively, as described above. In FIGS. 10 and 11 the cutting blade 70 is shown in a withdrawn position in which the distal end of the cutting blade is adjacent the proximal end regions 38 and 42 of the first and second jaws 18 and 20. In the position shown in FIGS. 10 and 11, the cutting blade 70 is not able to cut the tissue being held between the jaws 18 and 20. The cutting blade 70 is retained within a longitudinal slot in each jaw which guides the blade from the proximal end of the jaw towards the distal end of the jaw.

Figure 12:
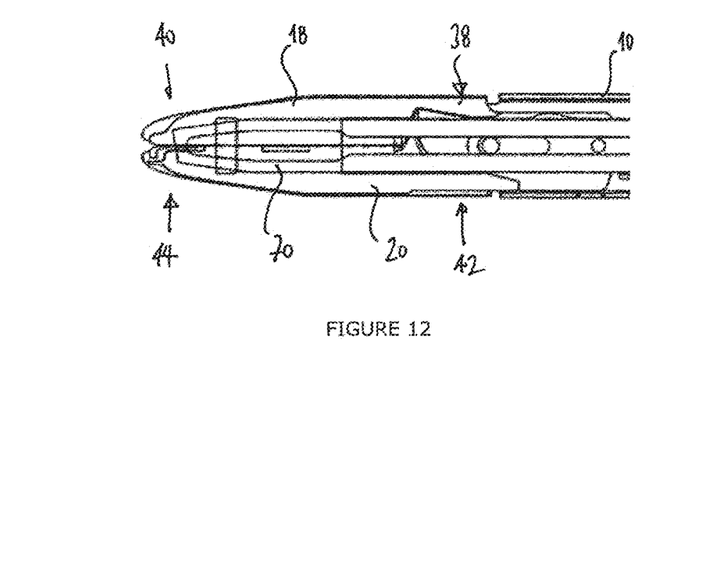
FIG. 12 is a side cross-sectional view of the part of FIG. 10 in a closed position illustrating a deployed position of the blade.

FIG. 12 illustrates the cutting blade 70 in a deployed position within the closed jaws 18 and 20. With reference to FIGS. 8 and 9, the cutting blade 70 is moved to this deployed position by the operator of the instrument squeezing the blade actuator 72 such that it rotates about the blade actuator pivot 74. In this manner, the cutting blade 70 is moved longitudinally along the elongate shaft 10, so that the distal end of the cutting blade moves towards the distal end regions 40 and 44 of the first and second jaws 18 and 20. As the cutting blade 70 moves to this position, it is able to make an appropriate cut of tissue held within the jaws 18 and 20.

Figure 13:
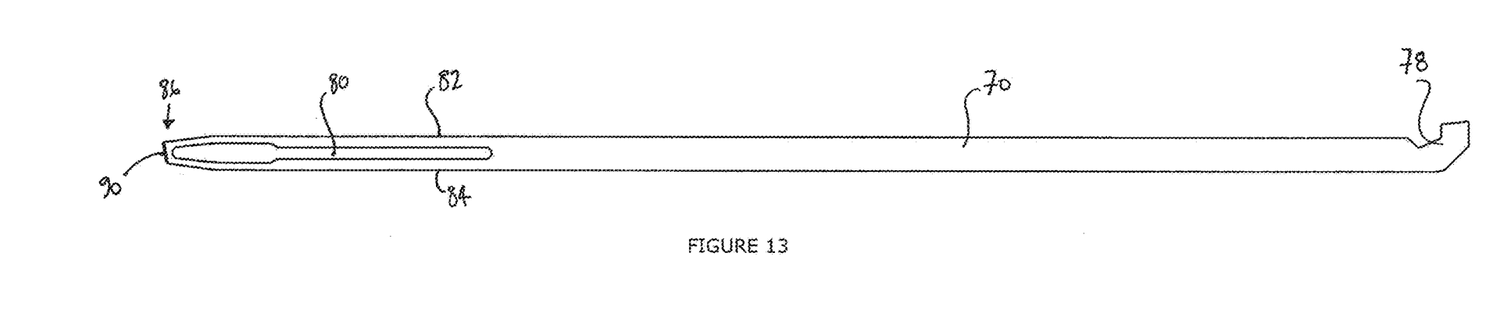
FIG. 13 is a side view of a blade embodying an aspect of the present invention.
Figure 14:
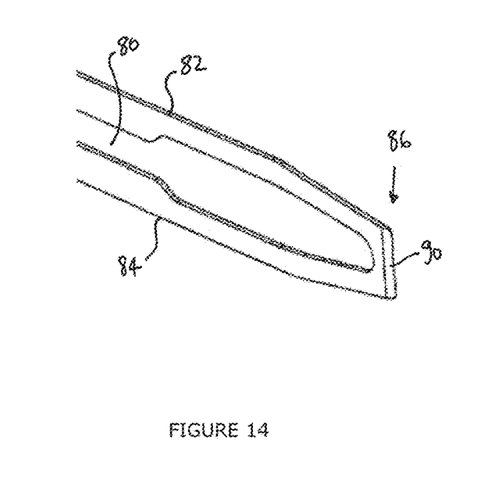
FIG. 14 is a perspective view of the blade of FIG. 13.
Figure 15:
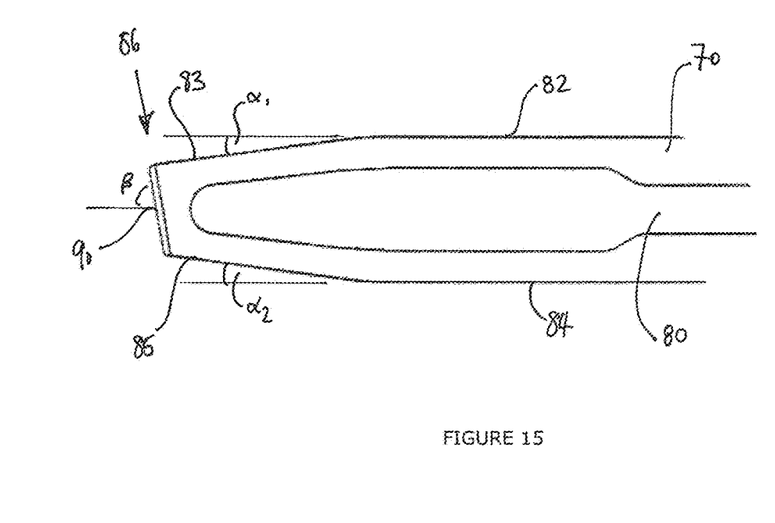
FIG. 15 is an enlarged side view of an end portion of the blade of FIG. 13.

FIGS. 13 to 15 illustrate a cutting blade embodying another aspect of the present invention. The cutting blade 70 is planar and elongate in nature and extends from the main housing 4 of the instrument 1 to the jaws 18 and 20 at the distal end of the elongate shaft 10. The cutting blade 70 extends through the elongate shaft 10. The distal end region of the cutting blade 70 is provided with a slot 80 through which the actuation pin 36 for the jaws 18 and 20, and any appropriate guide pins extend such arrangement allows the actuation of the jaws without the actuation of the cutting blade 70.

The cutting blade 70 has a first edge 82 and a second edge 84, which extend along the top and bottom of the plane are cutting blade 70 respectively. The cutting blade 70 reduces in height from a proximal end region 86 to a distal end region 88. That is, the distance between the first and second edges 82 and 84 decreases from the proximal end region 86 to the distal end region 88 of the cutting blade 70. The first and second edges 82 and 84 have respective portions 83 and 85 that extend at first and second acute angles $\alpha_1$ and $\alpha_2$ respectively with respect to the longitudinal axis of the cutting blade. Preferably, the first and second acute angles $\alpha_1$ and $\alpha_2$ are equal to one another.

A cutting surface 90 extends transversely with respect to the longitudinal axis of the cutting blade at the distal end thereof. The cutting surface 90 extends at a third angle $\beta$ to the longitudinal axis; the third angle $\beta$ is not equal to the first or second angle. Preferably, the cutting edge 90 is not perpendicular to the longitudinal axis, i.e. $\beta \neq 90°$.

Such a blade profile, with a distal end region which is narrower than the proximal end region, enables the provision of smaller jaws compared with previously-considered designs, whilst retaining the blade in position within the longitudinal slots in the jaws. The narrowed distal end region of the blade also the jaws to be closed correctly for the sealing process.

What is claimed is:

1. A substantially planar elongate cutting blade for a bipolar surgical instrument, the cutting blade defining a longitudinal axis with a proximal end and a distal end, the cutting blade having first and second opposed edges, the cutting blade comprising:
    a proximal end region which extends from the proximal end between the first and second edges over a first distance in a direction perpendicular to the longitudinal axis, a distal end region which extends from the proximal end region to the distal end; and
    a cutting edge at the distal end of the cutting blade, wherein:
        the first and second edges of the cutting blade have respective first and second distal end portions that extend along the distal end region to the cutting edge at the distal end of the cutting blade at fixed first and second acute angles respectively with respect to the longitudinal axis; and
        the cutting edge extends between the first and second distal end portions of the first and second edges over a second distance in the direction perpendicular to the longitudinal axis;
        the first distance is greater than the second distance, the cutting edge extends transversely at a third angle with respect to the longitudinal axis, the third angle is not equal to the first or second angle, and
        the cutting blade defines an elongate slot therethrough, the slot extending between the first and second distal end portions in a direction along the longitudinal axis and narrowing at the distal end region such that edges of the slot define acute angles relative to the longitudinal axis.

2. A cutting blade as claimed in claim 1, wherein the first acute angle is substantially equal to the second acute angle.

3. A cutting blade as claimed in claim 1, wherein the cutting edge is substantially centered on the longitudinal axis.

4. A bipolar surgical instrument comprising:
a body;
an elongate shaft attached to the body, the elongate shaft extending to a distal end;
first and second opposed jaws located at the distal end of the elongate shaft, the first jaw being movable with respect to the second jaw between an open position in which the first and second jaws are spaced apart from one another, and a closed position in which the first and second jaws are adjacent one another;
an actuation shaft connected with at least the first jaw, the actuation shaft being movable with respect to the body and the elongate shaft between a first position in which the jaws are in the open position, and a second position in which the jaws are in the closed position;
an actuation grip movably mounted on the body, and arranged to operate the actuation shaft, the actuation grip having a released position in which the actuation shaft is in the first position, and an engaged position in which the actuation shaft is in the second position; and
a blade as claimed in claim 1, the blade extending through the elongate shaft adjacent the actuation shaft, to the first and second jaws.

5. An instrument as claimed in claim 4, further comprising a blade actuator operable to move the blade between a retracted position and a cutting position.

6. An instrument as claimed in claim 4, wherein the jaws curve with respect to the elongate shaft.

* * * * *